(12) United States Patent
Griffin et al.

(10) Patent No.: US 7,288,102 B2
(45) Date of Patent: Oct. 30, 2007

(54) LANCING DEVICE WITH DECOUPLED LANCET

(75) Inventors: Carl E. Griffin, Marietta, GA (US); Avi M. Robbins, Longwood, FL (US); Michael V. Lipoma, Villa Rica, GA (US); David R. Buenger, Roswell, GA (US)

(73) Assignee: Facet Technologies, LLC, Kennesaw, GA (US)

( * ) Notice: Subject to any disclaimer, the term of this patent is extended or adjusted under 35 U.S.C. 154(b) by 586 days.

(21) Appl. No.: 10/806,029

(22) Filed: Mar. 22, 2004

(65) Prior Publication Data

US 2004/0249406 A1  Dec. 9, 2004

Related U.S. Application Data

(60) Provisional application No. 60/456,195, filed on Mar. 20, 2003.

(51) Int. Cl.
*A61B 17/14* (2006.01)

(52) U.S. Cl. ...................................... 606/182; 606/181

(58) Field of Classification Search ................ 606/181, 606/182, 183; 600/583; 604/156, 157
See application file for complete search history.

(56) References Cited

U.S. PATENT DOCUMENTS

| | | | | |
|---|---|---|---|---|
| 4,449,529 A | * | 5/1984 | Burns et al. ................ | 606/182 |
| 4,503,856 A | * | 3/1985 | Cornell et al. .............. | 606/182 |
| 4,527,561 A | * | 7/1985 | Burns ......................... | 606/182 |
| 4,535,769 A | * | 8/1985 | Burns ......................... | 606/182 |
| 4,553,541 A | * | 11/1985 | Burns ......................... | 606/182 |
| 4,616,649 A | * | 10/1986 | Burns ......................... | 606/182 |
| 4,817,603 A | * | 4/1989 | Turner et al. ................ | 606/182 |
| 4,895,147 A | | 1/1990 | Bodicky et al. | |
| 4,924,879 A | | 5/1990 | O'Brien | |
| 4,990,154 A | * | 2/1991 | Brown et al. ............... | 606/182 |
| 5,074,872 A | * | 12/1991 | Brown et al. ............... | 606/182 |
| 5,282,822 A | * | 2/1994 | Macors et al. .............. | 606/182 |
| 5,318,584 A | | 6/1994 | Lange et al. | |
| 5,368,047 A | * | 11/1994 | Suzuki et al. ............... | 600/578 |
| 5,569,287 A | * | 10/1996 | Tezuka et al. .............. | 606/182 |
| 5,613,978 A | | 3/1997 | Harding | |
| D379,516 S | | 5/1997 | Rutter | |
| 5,628,764 A | * | 5/1997 | Schraga ..................... | 606/182 |
| 5,730,753 A | | 3/1998 | Morita | |

(Continued)

OTHER PUBLICATIONS

Sutor et al., "Bleeding from Standardized Skin Punctures: Automated Technic for Recording Time, Intensity, and Pattern of Bleeding," Jou.C.P., vol. 55, May 1971, pp. 541-549.

(Continued)

*Primary Examiner*—Darwin P Erezo
(74) *Attorney, Agent, or Firm*—Gardner Groff Greenwald & Villanueva, PC

(57) ABSTRACT

A lancing device having a low-mass, high-velocity lancet decoupled from a drive mechanism when piercing a user's skin. The drive mechanism includes a spring-driven piston that impacts the lancet on firing to propel the lancet from a retracted position towards an extended position. After impact, but before the lancet reaches the extended position, a stop limits the travel of the piston to separate the piston from the lancet. Precise guidance of the lancet minimizes lateral movement of the lancet.

18 Claims, 8 Drawing Sheets

U.S. PATENT DOCUMENTS

| | | | |
|---|---|---|---|
| 5,741,288 A * | 4/1998 | Rife | 606/181 |
| 5,879,311 A | 3/1999 | Duchon et al. | |
| 5,885,211 A | 3/1999 | Eppstein et al. | |
| 5,908,434 A * | 6/1999 | Schraga | 606/181 |
| 5,916,230 A | 6/1999 | Brenneman et al. | |
| 5,964,718 A * | 10/1999 | Duchon et al. | 600/583 |
| 5,984,940 A | 11/1999 | Davis et al. | |
| 6,022,366 A | 2/2000 | Schraga et al. | |
| 6,045,567 A | 4/2000 | Taylor et al. | |
| 6,056,701 A * | 5/2000 | Duchon et al. | 600/583 |
| 6,066,103 A * | 5/2000 | Duchon et al. | 600/583 |
| 6,086,545 A * | 7/2000 | Roe et al. | 600/570 |
| 6,156,050 A | 12/2000 | Davis et al. | |
| 6,156,051 A | 12/2000 | Schraga | |
| 6,283,982 B1 | 9/2001 | Levaughn et al. | |
| 6,322,575 B1 | 11/2001 | Schraga | |
| 6,451,040 B1 | 9/2002 | Purcell | |
| 6,464,649 B1 * | 10/2002 | Duchon et al. | 600/583 |
| 6,530,937 B1 | 3/2003 | Schraga | |
| 6,558,402 B1 | 5/2003 | Chelak et al. | |
| 6,730,046 B1 * | 5/2004 | Hamamoto et al. | 600/583 |
| 6,949,111 B2 * | 9/2005 | Schraga | 606/182 |
| 6,969,359 B2 * | 11/2005 | Duchon et al. | 600/583 |
| 2001/0027327 A1 | 10/2001 | Schraga | |
| 2002/0029059 A1 | 3/2002 | Purcell | |
| 2003/0018282 A1 | 1/2003 | Effenhauser et al. | |
| 2003/0088261 A1 | 5/2003 | Schraga | |
| 2003/0225430 A1 | 12/2003 | Schraga | |

OTHER PUBLICATIONS

Bayer, "Ames Glucolet" lancing device; 2 pgs.
Bayer, "Microlet" lancing device; 2 pgs.
Bayer, "Vaculance" lancing device, 1 pg.
Bechton-Dickinson, "Autolance" lancing device; 2 pgs.
Lifescan/Johnson & Johnson, Penlet Plus, lancing device; 2pgs.
Lifescan, "Penlet II" lancing device; 2 pgs.
Palco, "Auto-Lancet" lancing device; 2 pgs.
Roche, "Autoclix" lancing device 2 pgs.
Roche, Soft Touch II lancing device; 1 pg.

* cited by examiner

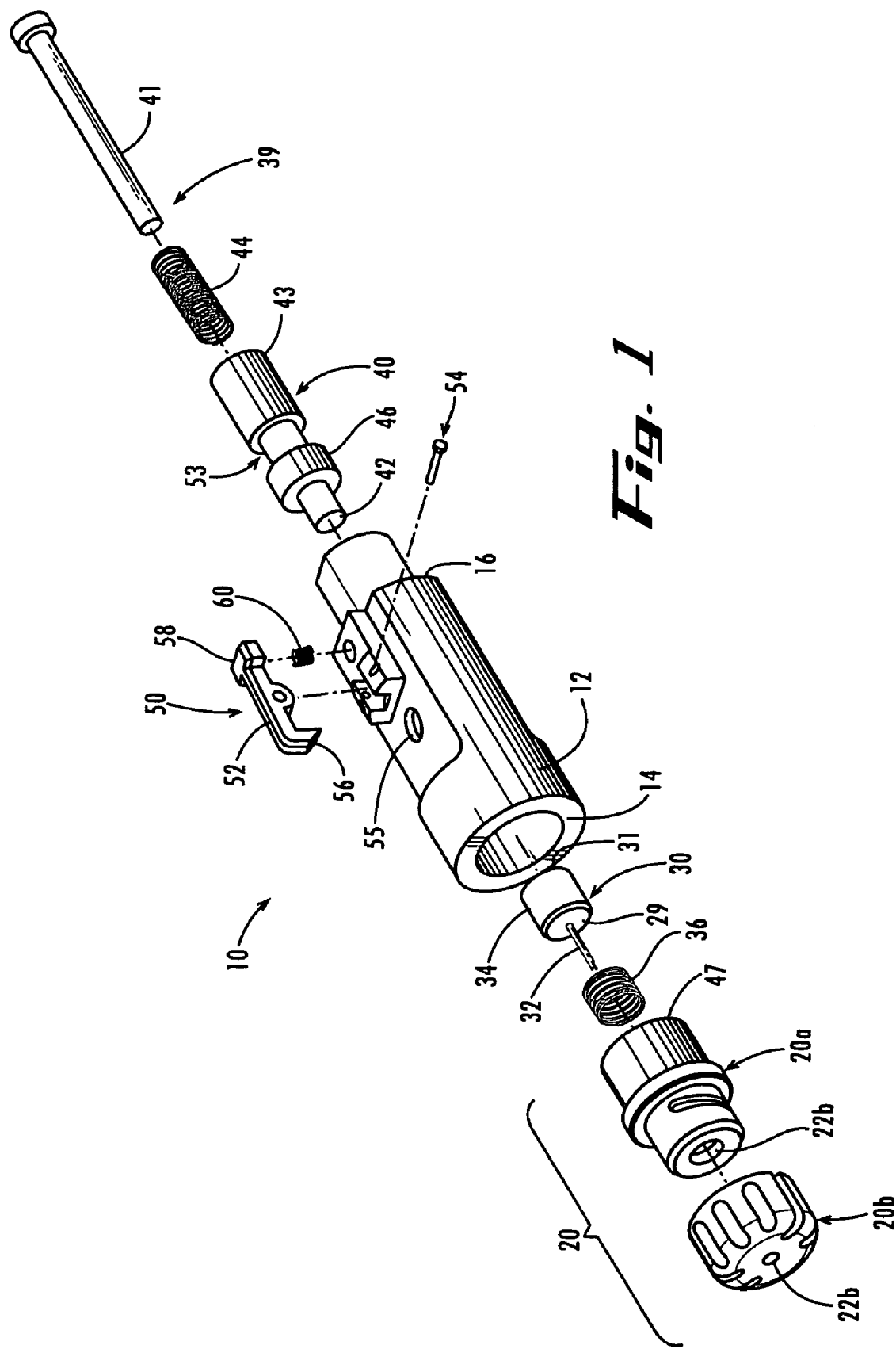

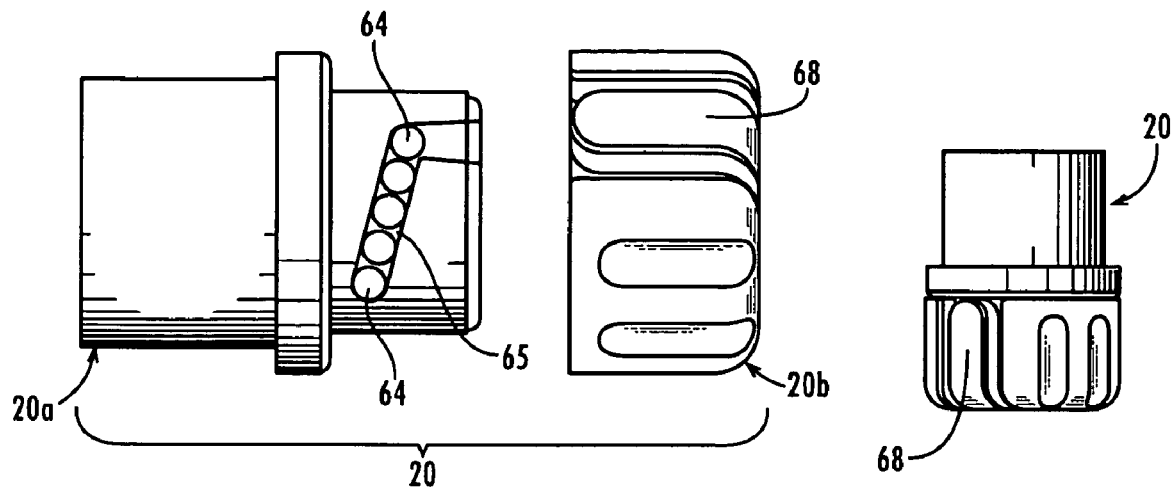
*Fig. 8*     *Fig. 9*
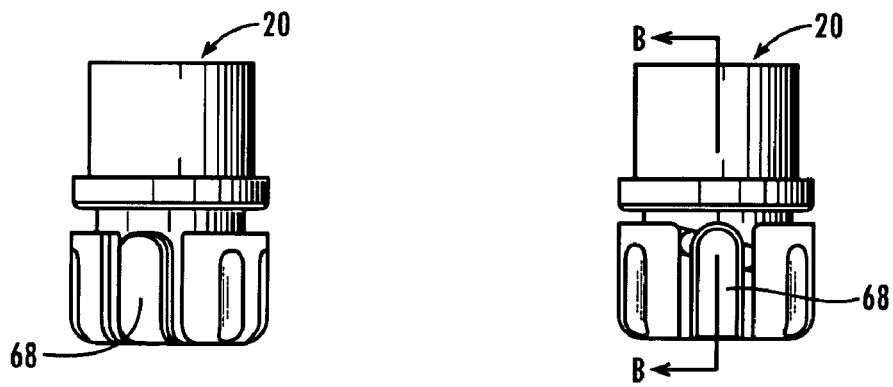
*Fig. 10*     *Fig. 11*
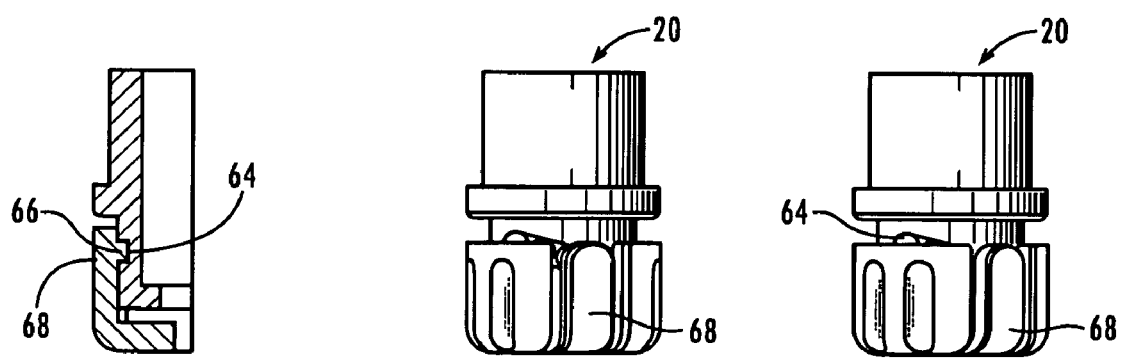
*Fig. 12*     *Fig. 13*     *Fig. 14*

LANCING DEVICE WITH DECOUPLED LANCET

CROSS-REFERENCE TO RELATED APPLICATION

This application claims the priority benefit of U.S. Provisional Application Ser. No. 60/456,195, filed Mar. 20, 2003, which is hereby incorporated by reference herein.

FIELD OF THE INVENTION

The present invention relates generally to the field of medical sampling devices, and more particularly to a lancing device including a high-velocity, low-mass lancet, and a drive mechanism decoupled from the lancet during the lancing operation.

BACKGROUND OF THE INVENTION

Various lancing devices are known for penetrating the skin of a human or animal subject at a lancing site for obtaining a sample of blood or other body fluids. In general, a typical lancing device includes a housing containing a lancet connected to a spring-driven drive mechanism, and further includes a cocking mechanism for arming or energizing the drive-spring, and a trigger mechanism for releasing the drive mechanism to complete the lancing operation.

In order to encourage compliance with a prescribed sampling regimen, for example as in blood glucose sampling by diabetics, it is desirable to minimize the pain and discomfort resulting from the lancing procedure. To date, efforts to minimize pain from lancing have largely focused on controlling the depth of penetration into the subject's skin at the lancing site. For example, many lancing devices include a depth-control mechanism for varying the depth of penetration, either by adjusting the distance of travel of the lancet tip, or by adjusting the position of an endcap through which the lancet protrudes during the lancing operation.

Advances in lancing device technology have, to some extent, reduced the pain associated with the lancing process. However, continued improvement in reducing pain and discomfort associated with the lancing process is a continuing need. It is to an improved lancing device meeting this and other needs that the present invention is primarily directed.

SUMMARY OF THE INVENTION

The present invention provides an improved lancing device for reducing pain and discomfort associated with the lancing process. Advantageously, example forms of the present invention minimize pain by reducing the mass behind the lancet and increasing its velocity as it pierces the skin of the subject at the lancing site. This reduction in mass and increased velocity is achieved, at least in part, by decoupling the lancet from the drive mechanism for the lancet, during at least that portion of the lancet travel when the lancet tip pierces the skin at the sampling site. Example embodiments of the present invention further minimize pain and trauma by enabling improved control and more precise guidance of the lancet to minimize or prevent lateral movement of the lancet during puncture.

In one aspect, the present invention is a multi-use or disposable lancing device. The device preferably includes a lancet movable between a retracted position and an extended position, and a drive member for impacting the lancet to drive the lancet from the retracted position to the extended position, wherein the drive member is decoupled from the lancet when the lancet is in its extended position.

Preferably, the lancing device includes a stop member that limits the travel of the drive member before the lancet reaches the extended position. But the drive member stop does not limit the travel of the lancet. So the lancet decouples from the drive member and continues moving toward the extended position after the drive member is stopped by the drive member stop. In addition, the lancing device preferably includes a separate stop member that limits the travel of the lancet in the extended position.

In example embodiments, the lancing device includes a drive spring nested within an opening in the drive member so that part of the drive spring is closer to the lancet that part of the drive member, thereby reducing lateral movement of the drive member and lancet. The lancing device further includes a trigger mechanism for holding the drive member in the retracted position and releasing the drive member for movement to the extended position, with the trigger mechanism having a latch that is removably engages a notch in the drive member. Also, the drive member comprises a ram or piston, which has a greater mass than the lancet.

Furthermore, example embodiments of the invention include a penetration depth adjustment feature. For example, the lancing device may be provided with an endcap comprising an inner cap and an outer cap that rotates relative to the inner cap. The inner cap has a helical channel with a series of recesses that sequentially receive a protrusion on a flexible arm of the outer cap. In this way, rotating the outer cap moves it axially between discrete penetration depth settings.

In another aspect, the present invention is a method of lancing the skin to sample body fluid. The method preferably includes impacting a low-mass lancet with a drive member to move the low-mass lancet from a retracted position to an extended position; and decoupling the motion of the low-mass lancet from the motion of the drive member through at least a portion of a path of travel of the lancet.

These and other aspects, features, and advantages of the invention will be understood with reference to the drawing figures and detailed description herein, and will be realized by means of the various elements and combinations particularly pointed out in the appended claims. It is to be understood that both the foregoing general description and the following brief description of the drawings and detailed description of the invention are exemplary and explanatory of preferred embodiments of the invention, and are not restrictive of the invention, as claimed.

BRIEF DESCRIPTION OF THE DRAWING FIGURES

FIG. 7 is a cross-sectional view of the lancing device of FIG. 1, in an extended or puncturing position, with the lancet decoupled from the piston.

FIG. 8 is an exploded side view of an endcap of the lancing device of FIG. 1, showing an inner cap and an outer cap.

FIG. 9 is a side view of the endcap of FIG. 8, showing the outer cap assembled onto the inner cap in a first depth position.

FIG. 10 is a side view of the endcap of FIG. 8, showing the outer cap rotated to a second depth position.

FIG. 11 is a side view of the endcap of FIG. 8, showing the outer cap rotated to a third depth position.

FIG. 12 is a cross-sectional view of a portion of the endcap taken at line B-B of FIG. 11.

FIG. 13 is a side view of the endcap of FIG. 8, showing the outer cap rotated to a fourth depth position.

FIG. 14 is a side view of the endcap of FIG. 8, showing the outer cap rotated to a fifth depth position.

DETAILED DESCRIPTION OF EXAMPLE EMBODIMENTS

Figure 2:
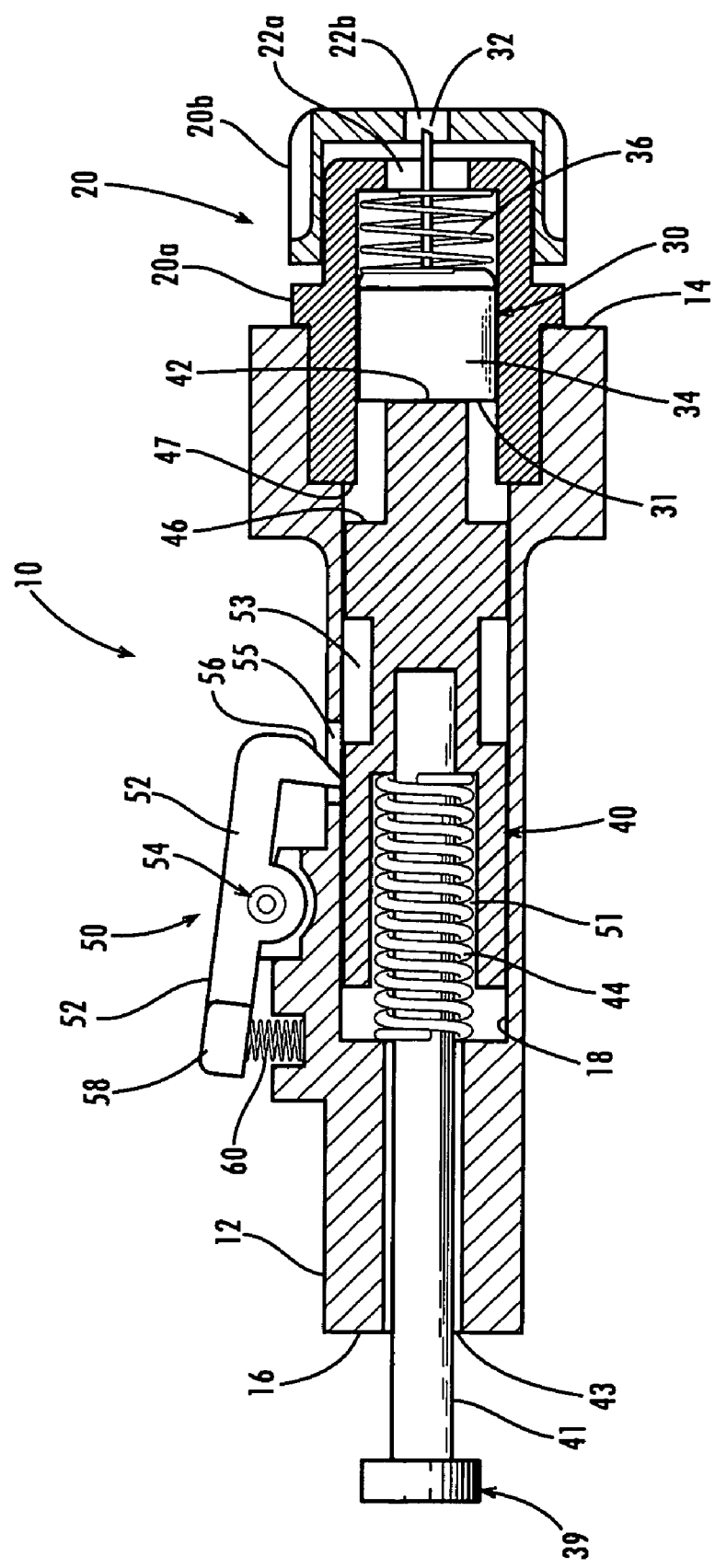
FIG. 2 is a cross-sectional view of the lancing device of FIG. 1, in an uncocked, rest position.

Referring now to the drawing figures, wherein like reference numerals represent like parts throughout, preferred forms of the present invention will now be described. It is to be understood that this invention is not limited to the specific devices, methods, conditions, or parameters described and/or shown herein, and that the terminology used herein is for the purpose of describing particular embodiments by way of example only. Thus, the terminology is intended to be broadly construed and is not intended to be limiting of the claimed invention. In addition, as used in the specification including the appended claims, the singular forms "a," "an," and "the" include the plural, plural forms include the singular, and reference to a particular numerical value includes at least that particular value, unless the context clearly dictates otherwise. Furthermore, any methods described herein are not intended to be limited to the sequence of steps described but can be carried out in other sequences, unless expressly stated otherwise herein.

Figure 1:
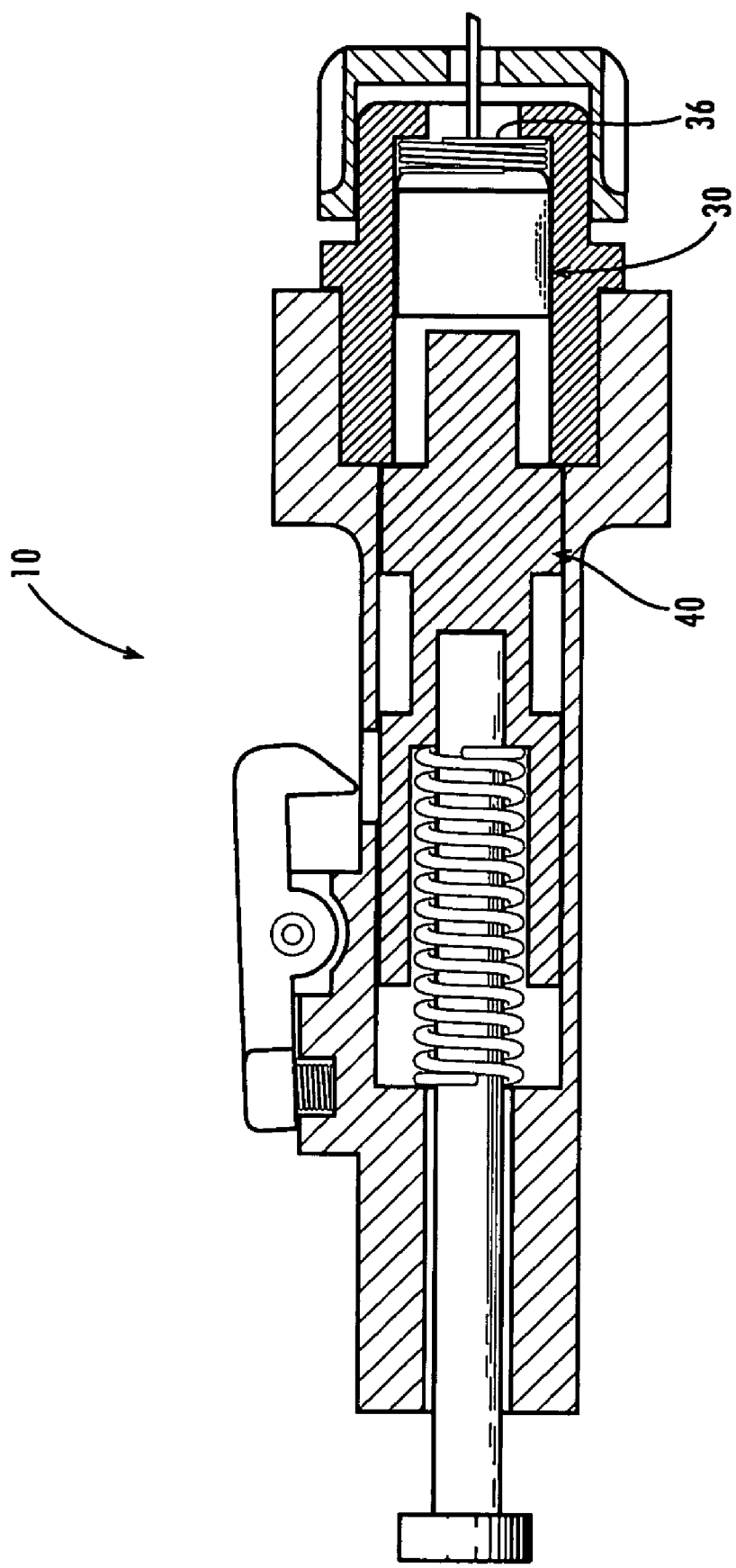
FIG. 1 is an exploded perspective view of a lancing device according to an example embodiment of the present invention.

FIGS. 1 and 2 show the major components of a lancing device 10 according to an example embodiment of the present invention. The lancing device 10 preferably comprises an outer shell or housing 12. The housing 12 may be, for example, a generally cylindrical element having a proximal end 14 and a distal end 16, and defining an axial interior chamber 18 extending substantially through its length from end to end. The housing 12 is preferably formed of plastic and/or another substantially rigid material(s), for example by injection molding.

The lancing device 10 preferably includes an endcap 20 mounted to the proximal end 14 of the housing. Preferably, the endcap 20 includes an inner cap member 20a and an outer cap member 20b for providing lancing depth adjustment capability, as described in detail with reference to FIGS. 8-14. The endcap 20 cooperatives with the housing 12 to define the axial interior chamber 18. In addition, the endcap 20 preferably includes an opening or passage through which a lancing tip extends for puncturing. For example, the inner and outer caps 20a and 20b may include aligned openings or passages 22a and 22b (collectively, "the opening 22"). Also, depth indicia and/or sample size indicia may be provided on the endcap 20 and/or the housing 12 to indicate the lancing depth setting.

In an alternative embodiment, the endcap is a single piece that is separate from and attached to the housing. And in another alternative embodiment, the endcap is integrally formed with the housing into a single piece without depth adjustment capability, that is, the endcap is essentially an endwall of the housing. As such, the term "endcap" as used herein includes any structure at the proximal end of the housing, whether separate from or integral to the housing.

In still other alternative embodiments, the lancing device enables depth adjustment by other mechanisms. For example, the endcap may have one or more adjustably positionable internal stop members that limit the distance of travel of a lancet, or the endcap may be adjustable so that the axial position of the endcap may be varied to limit the travel. In particular, the endcap can be joined to the housing by a threaded connection permitting the endcap to be extended and retracted axially relative to the housing by twisting the endcap. And in yet other alternative embodiments, a proximal face of the endcap has one or more raised projections or rings for stimulating bloodflow for sample collection, as by pressure and/or pumping, and/or may be transparent or comprise a transparent portion for monitoring sample collection.

A lancet 30 is preferably slidably mounted within the housing 12 and/or the endcap 20, for translation between a retracted position within the housing and endcap, and an extended position wherein a sharp lancing tip portion 32 of the lancet projects through the opening 22 in the endcap 20. A close sliding fit is preferably provided between the lancet 30 and the housing 12 and/or the endcap 20 to minimize lateral movement and rocking of the lancing tip 32 during the lancing operation. The lancet 30 preferably comprises a body portion 34 formed of plastic and/or another material(s), having a proximal end 29 from which the lancing tip 32 projects and a distal end 31 opposite the proximal end. The body portion 34 of the lancet 30 is preferably larger in at least one dimension than the opening 22 to prevent the lancet from passing through the opening and being discharged from the housing 12 and endcap 20. For example, the lancet 30 may be provided with the proximal end 29 of the body portion 34 dimensioned so that it will not pass through the endcap opening 22, but will instead engage the endcap 20 to limit the travel of the lancet. The lancet 30 may be substantially smaller and lighter in weight than standard known lancets, because the lancet does not need to incorporate a gripping surface or engagement features for coupling the lancet with the drive mechanism of the lancing device 10. A return spring 36 is preferably engaged between the lancet 30 and the endcap 20 or housing 12 to retract the lancing tip 32 back into a shielded position after lancing, enclosed within the housing and endcap, to prevent inadvertent needlesticks or bloodborne contamination.

A drive mechanism includes a drive member such as a ram or piston 40 that is preferably mounted to translate axially within the chamber 18 of the housing 12 and/or endcap 20. The piston 40 preferably includes a proximal end 42 for impacting the distal end 31 of the lancet 30 upon firing to propel the lancet into its extended or lancing position, for puncturing the skin of the subject at the lancing site. The contacting surfaces of the piston 40 and the lancet 30 are preferably smooth, parallel surfaces, or provide point contact at the approximate centerpoint of the lancet, to minimize or prevent lateral movement or rocking of the lancet during the lancing procedure. The piston 40 is preferably sized and shaped to generally conform to the inner shaped of the axial interior chamber 18 of the housing 12 and/or endcap 20 with a nice fit for preventing or eliminating lateral movement. In a typical commercial embodiment, for example, the piston 40 and the axial interior chamber 18 are generally cylindrical. In addition, the center of mass of the piston 40 is preferably axially aligned with the center of mass of the lancet 30, further minimizing lateral movement or rocking of the lancet. And the mass of the piston 40 is preferably greater than that of the lancet 30, which reduces the mass of the components impacting and piercing the skin.

A cocking mechanism 39 preferably includes an arm or rod 41 that extends from the piston 40 to a position external of the housing 12, for example through an opening 43 in the distal end 16 of the housing 12 as shown, or alternatively through a side or other opening formed in the housing. The cocking rod 41 may be a separate component affixed or coupled to the piston 40. For example, the cocking rod 41 may be fixedly received in an opening 51 in the piston 40, as shown. Alternatively, the cocking rod 41 may be integrally formed with the piston 40 as a single component.

The drive mechanism preferably further includes a drive spring 44 for driving the piston 40 from a retracted position to an extended position for impacting the lancet 30. The drive spring 44 may be engaged between the piston 40 and the housing 12, for example received in the piston opening 51 as shown, or between the cocking rod 42 and the housing. With the drive spring 44 received in the opening 51 of the piston 40, the proximal end of the drive spring is forward (closer to the lancet) of the distal end of the piston so that it is not "pushing" the piston from behind, thereby helping to reduce any lateral movement of the piston in the chamber 18 and generally providing improved guidance and control. It will be understood that the lancing device 10 may be alternatively provided with a different cocking mechanism, or without a cocking mechanism for single-use lancing devices.

The piston 40 preferably comprises a flared shoulder, projection, or segment 46 having an expanded dimension for contacting a stop or limit member to limit the travel of the piston during the lancing operation. For example, the stop or limit member may be provided by a distal face portion 47 of the endcap 20, or alternatively by an interference member projecting from another part of the housing 12 or endcap 20, or by another component of the lancing device 12. In addition, the piston 40 has another flared shoulder, projection, or segment 43, with the opening 51 preferably defined therein. The flared segments 43 and 46 of the piston 40 together define a locking notch 53. The locking notch 53 may be a circumferential channel, as shown, or it may be a circular hole or otherwise configured notch.

The lancing device 10 preferably further comprises a trigger mechanism 50. For example, in the depicted embodiment, a rocker arm 52 is pivotally mounted to the housing 12 by a hinge or other pivotal connection 54 approximately midway along the length of the rocker arm. A latch 56 extends from a proximal end of the rocker arm 52, and through an opening 55 in the sidewall of the housing 12 to engage and release the piston 40 during cocking and firing. A release button or contact surface 58 is provided on the distal end of the rocker arm 52, for selectively releasing the trigger mechanism when the user is ready to fire the device and carry out a lancing sequence. A spring 60 normally biases the latch end of the rocker arm 52 inward for engagement with a shoulder defined by the notch 53 of the piston 40 during cocking, until the user overcomes the biasing force of the spring by applying finger pressure onto the release button 58 to pivot the latch 56 out of engagement with the lock notch to fire the lancing device 10. It will be understood that the lancing device 10 may be alternatively provided with a different trigger mechanism.

FIGS. 2-7 depict a sequence of operation of the lancing device 10 and a method of lancing according to an example embodiment of the present invention. The lancing device 10 is initially delivered to the user in an uncocked, rest position, as shown in FIG. 2. The opening 22 in the endcap 20 may initially be sealed for sterility, as by a penetrable foil covering, or by a plug or cap that is removed by the user prior to use.

Figure 3:
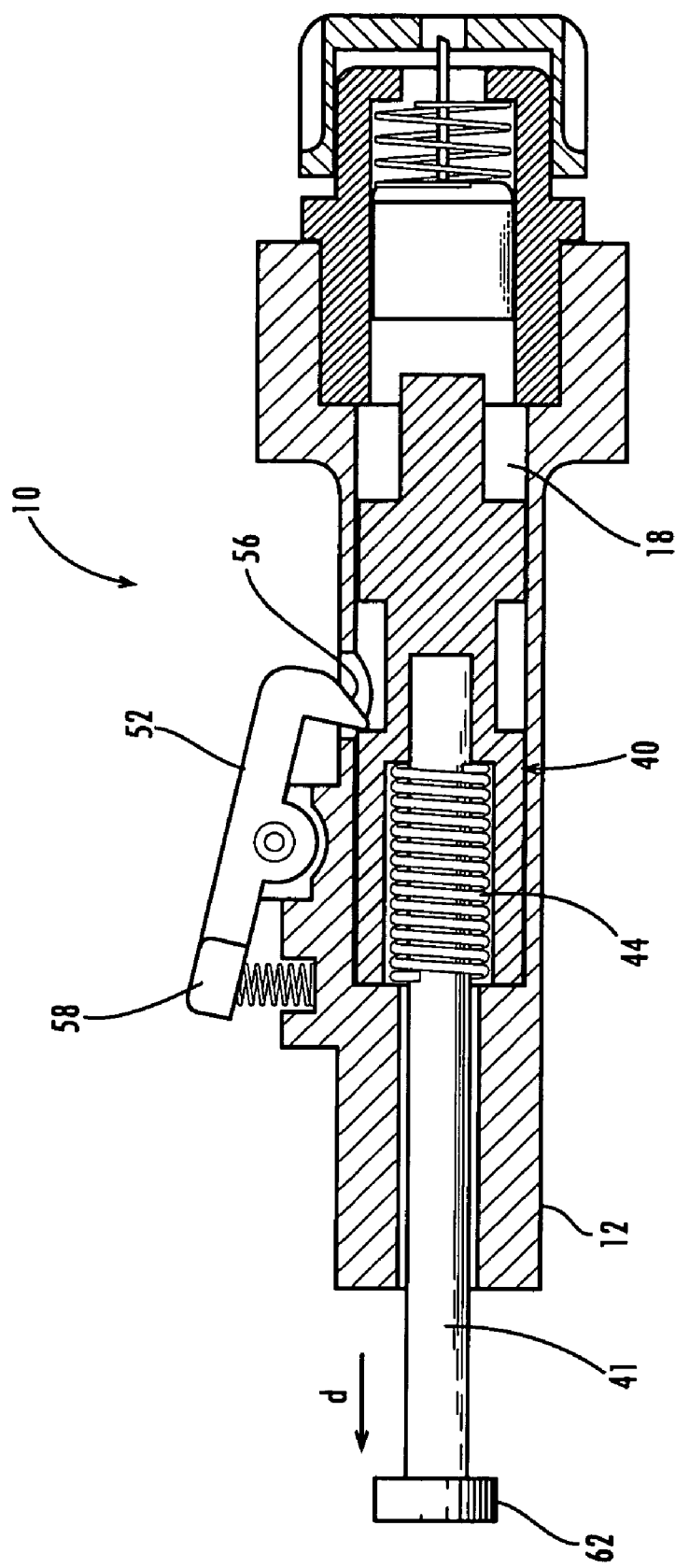
FIG. 3 is a cross-sectional view of the lancing device of FIG. 1, in a cocked or armed position.
Figure 4:
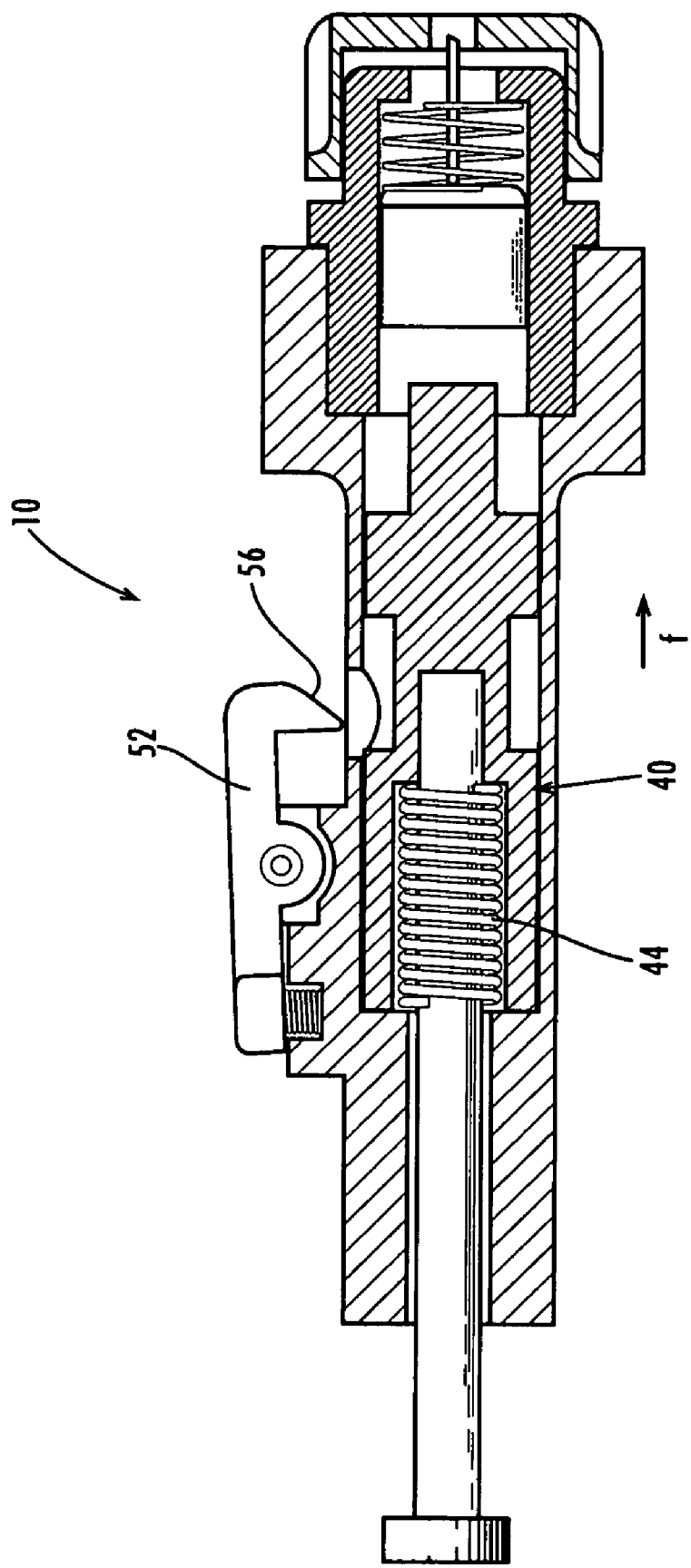
FIG. 4 is a cross-sectional view of the lancing device of FIG. 1, in a firing or activated position.

The user cocks the device 10 to the cocked or armed position of FIG. 3 by grasping the cocking rod 41 and drawing it away from the housing 12 in the distal direction indicated by direction arrow "d." The cocking rod 41 preferably includes a knob 62 or other gripping surface to make cocking easier. As the cocking rod 41 is drawn back, the piston 40 is also retracted axially through the chamber 18 of the housing 12, compressing and energizing the drive-spring 44, until the latch 56 of the rocker arm 52 engages the notch 53 of the piston 40 to retain the piston in the cocked or armed position, as shown in FIG. 3.

Figure 5:
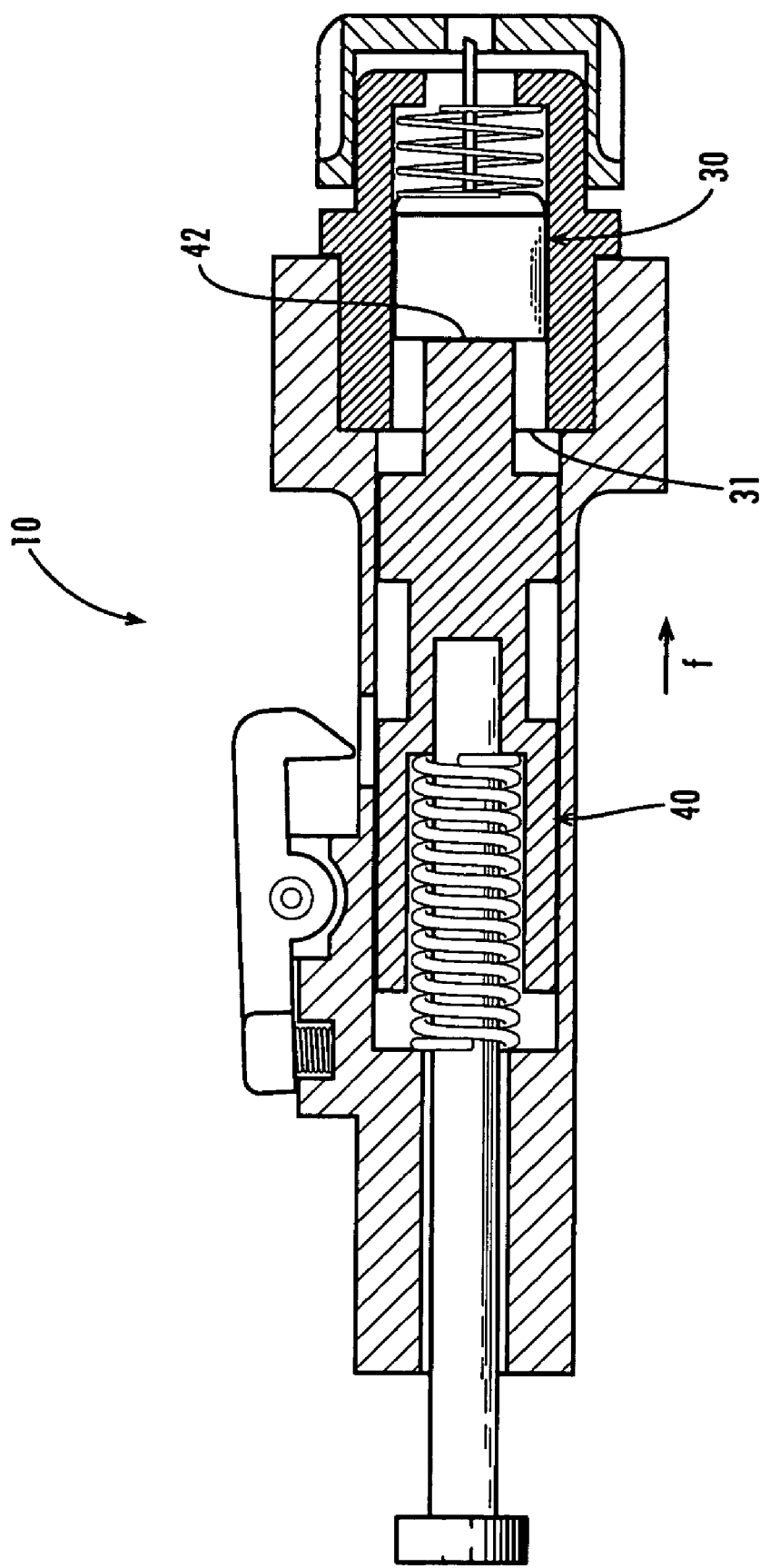
FIG. 5 is a cross-sectional view of the lancing device of FIG. 1, in a piston/lancet impact position.
Figure 6:
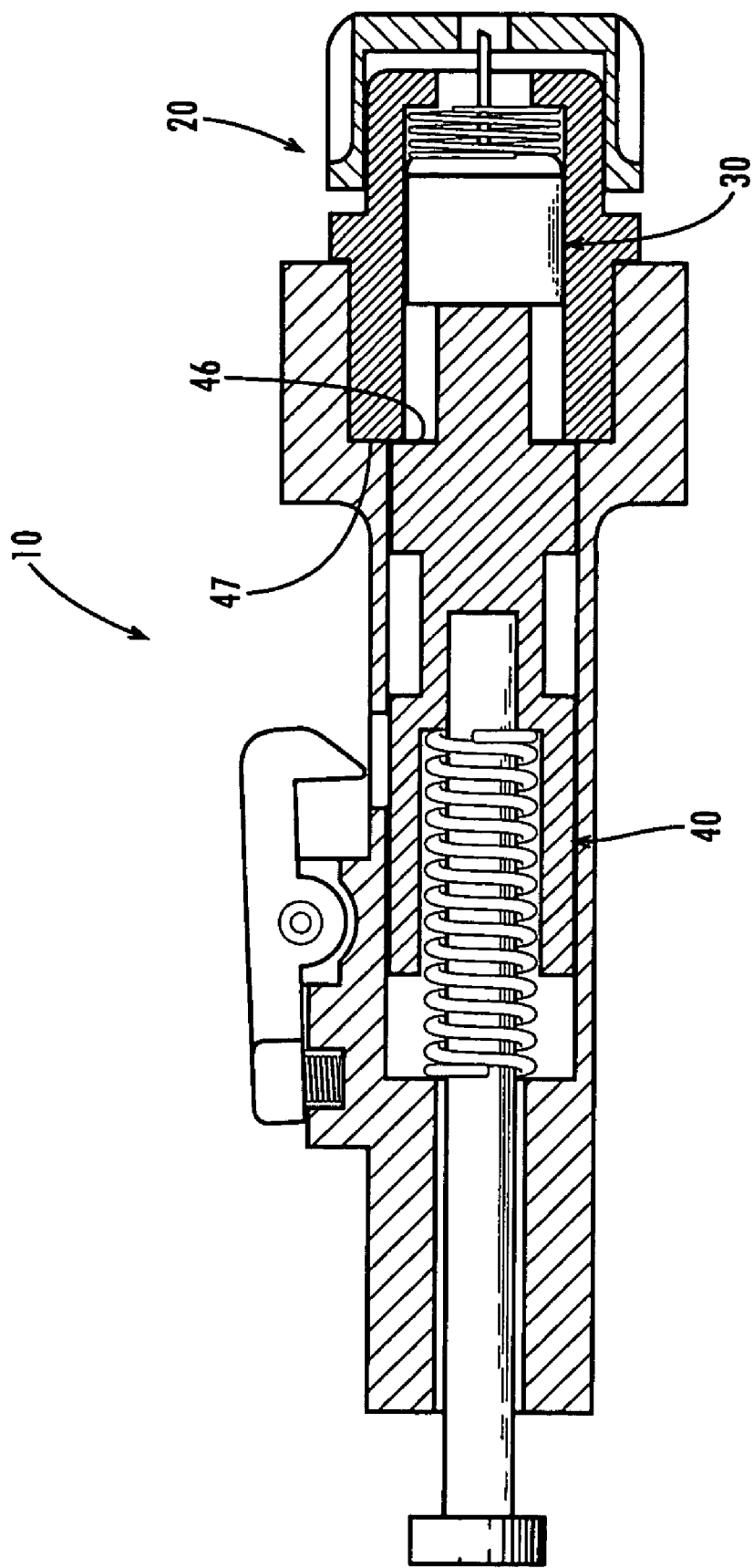
FIG. 6 is a cross-sectional view of the lancing device of FIG. 1, in a piston stop position, just before decoupling.

The user then places the proximal face of the lancing device 10 into contact with the skin at the sampling site and presses the release button 58. This draws the latch 56 out of engagement with the piston 40, releasing the piston to be driven by the drive spring 44 in the firing direction indicated by direction arrow "f" in FIG. 4. The proximal end 42 of the piston 40 then impacts the distal end 31 of the lancet 30, as shown in FIG. 5, and propels the lancet 30 in the firing direction "f." After the piston 40 impacts the lancet 30, the expanded segment 46 of the piston contacts the distal face 47 of the endcap 20 to stop the travel of the piston, as shown in FIG. 6. The lancet 30 is thereby decoupled from the piston 40 as the lancet continues on until it is stopped by a stop or limit member in its extended or lancing position, as shown in FIG. 7. The lancet stop may be defined by the inside wall of the endcap or another structure. In any case, the lancet stop and the drive member stop are two separate structures, that is, they are not one and the same (even though they may both be defined by the endcap or the housing or another component of the lancing device).

By decoupling the lancet 30 from the drive mechanism, the mass of the components coupled to the lancet when the skin is pierced is reduced, which has been found to minimize the sensation of pain experienced by the subject. Just before the piston 40 impacts the lancet 30, the piston has kinetic energy and the lancet does not. And just after the piston 40 impacts the stop 47, the lancet has kinetic energy and the piston does not. After the lancet 30 is driven into its extended position to puncture the skin at the sample site, the return spring 36 returns the lancet to the retracted position wherein the lancet tip is protected from inadvertent contact.

Turning now to FIGS. 8-14, there are shown additional details of the inner and outer caps 20a and 20b of the endcap 20. As shown in FIGS. 8 and 12, the inner cap 20a has a helical channel 65 with a series of recesses 64 that receive a protrusion 66 on a flexible arm 68 of the outer cap 20b. As the user rotates the outer cap 20b, the protrusion 66 on the flexible arm 68 rides in the helical channel 65, thereby moving the endcap 20 axially and changing the penetration depth. The protrusion 66 seats in the recesses 64 to provide discrete depth settings, and the flexible arm 68 deflects when the protrusion is between the recesses 64 to permit adjusting between the depth settings. Any number of depth settings may be provided, space permitting. In the embodiment shown, there are five recesses 64, which provide five discrete depth settings. FIGS. 9, 10, 11, 13 and 14 show these five depth settings, progressing from the deepest to the shallowest.

To replace the lancet 30 in the lancing device 10, the user removes the endcap 20 from the housing 12, with the return spring 36 retained in the endcap. The used lancet 30 is then removed and a fresh one inserted. To do this, the user can grasp the lancet body 34, instead of the lancet tip 32, and insert the lancet 30 into the endcap 20 tip-first. Then the endcap 20, now holding the lancet 30 and the return spring 36, is replaced on the housing 12, ands the lancing device is ready for another use. The process can be repeated as needed for subsequent lancings.

In alternative embodiments, the decoupled drive member is provided by a spring-biased rocker, hammer, or punch, or a transversely driven cam surface, instead of the piston. In another alternative embodiment, the piston stop member extends from the housing, instead of the endcap, to retain the piston in the housing when the endcap is removed for lancet replacement. And in another alternative embodiment, the piston stop member is located closer to the proximal end of the lancing device, and the shoulder of the piston that engages the stop member is defined by the proximal face of the drive member, so that substantially the entire length of the piston is in sliding contact in the axial chamber to minimize lateral movement.

Accordingly, it can be seen that the present invention provides advantages over other lancing devices. In particular, the present invention includes lancing devices in which the drive mechanism is decoupled from lancet when the skin is pierced. Because of this decoupling, there is less mass behind the lancet tip when impacting the skin, which reduces the pain felt by the user. In addition, the drive spring is decoupled from the lancet when the skin is pierced, thereby preventing restrikes from spring-induced lancet oscillations. Furthermore, the lancet has a high velocity relative to previous lancing devices because of the reduced mass/energy ratio from decoupling the lancet from the drive mechanism.

It should be understood that the foregoing relates only to example embodiments of the present invention, and that numerous changes, additions, modifications and deletions may be made from the example embodiments described without departing from the spirit and scope of the invention as defined by the following claims.

What is claimed is:

1. A lancing device for puncturing skin, comprising:
a lancet movable between a retracted position and an extended position;
a drive member that is forwardly movable to impact the lancet to drive the lancet forward from the retracted position toward the extended position; and
a drive member stop member that stops the forward travel of the drive member before the lancet reaches the extended position,
wherein the drive member stop member does not stop the forward travel of the lancet and the lancet decouples from the drive member and continues moving forward under its own momentum toward the extended position after the drive member is stopped by the drive member stop member, wherein the drive member is decoupled from the lancet from before the lancet reaches the extended position at least until the lancet is in the extended position so that the mass of the drive member is not bearing on the lancet when the lancet punctures the skin.

2. The lancing device of claim 1, further comprising a lancet stop member that limits the travel of the lancet in the extended position, the lancet stop member being a separate structure from the drive member stop member.

3. The lancing device of claim 1, wherein the drive member comprises a ram or piston.

4. The lancing device of claim 1, wherein the drive member includes a distal end defining an opening, and further comprising a drive spring that is received in the drive member opening, a housing for the drive member and the lancet, and a cocking mechanism including an arm or rod that extends from the drive member to external of the housing, wherein when the cocking arm/rod is operably moved the drive member is retracted and the drive spring is compressed within the drive member opening, and when the lancing device is activated the drive spring discharges within the drive member opening to launch the drive member toward the lancet, wherein a proximal end of the drive spring is closer to the lancet than the distal end of the drive member so that the drive spring does not push the drive member from the drive member distal end.

5. The lancing device of claim 1, further comprising a trigger latch that is removably receivable in a notch in the drive member.

6. The lancing device of claim 1, further comprising an endcap with at least a portion that rotates to adjust a penetration depth of the lancet.

7. The lancing device of claim 1, further comprising a return spring that, after the lancet is driven to the extended position to puncture the skin, returns the lancet toward the retracted position, into engagement with the drive member, and into a rest position.

8. A lancing device comprising:
a lancet movable between a retracted position and an extended position;
a drive member that impacts the lancet to drive the lancet from the retracted position to the extended position, wherein the drive member is decoupled from the lancet when the lancet is in the extended position;
a drive member stop member that limits the travel of the drive member before the lancet reaches the extended position, wherein the drive member stop member does not limit the travel of the lancet and the lancet decouples from the drive member and continues moving under its own momentum toward the extended position after the drive member is stopped by the drive member stop member; and
a lancet stop member that limits the travel of the lancet in the extended position, the lancet stop member being a separate structure from the drive member stop member.

9. The lancing device of claim 8, wherein the drive member comprises a ram or piston.

10. The lancing device of claim 8, wherein the drive member includes a distal end defining an opening, and further comprising a drive spring that is received in the drive member opening, a housing for the drive member and the lancet, and a cocking mechanism including an arm or rod that extends from the drive member to external of the housing, wherein when the cocking arm/rod is operably moved the drive member is retracted and the drive spring is compressed within the drive member opening, and when the lancing device is activated the drive spring discharges within the drive member opening to launch the drive member toward the lancet, wherein a proximal end of the drive spring is closer to the lancet than the distal end of the drive member so that the drive spring does not push the drive member from the drive member distal end.

11. The lancing device of claim 8, further comprising a trigger mechanism for holding the drive member in the retracted position and releasing the drive member for movement to the extended position, wherein the trigger mechanism comprises a latch that is removably receivable in a notch in the drive member.

12. The lancing device of claim 11, further comprising a cocking mechanism for moving the drive member to the retracted position.

13. The lancing device of claim 8, further comprising an endcap with at least a portion that rotates to adjust a penetration depth of the lancet.

14. The lancing device of claim 13, wherein the endcap comprises an inner cap and an outer cap that rotates relative to the inner cap, the inner cap having a helical channel with a series of recesses that sequentially receive a protrusion on a flexible arm of the outer cap, wherein rotating the outer cap moves it axially between discrete penetration depth settings.

15. The lancing device of claim 8, wherein the drive member and the lancet are configured so that, just before the drive member impacts the lancet, the drive member has kinetic energy and the lancet does not have any kinetic energy, and just after the drive member impacts the drive member stop member, the lancet has kinetic energy and the drive member does not have any kinetic energy.

16. A method of lancing skin to sample body fluid, comprising:

impacting a lancet with a drive member to move the lancet forward from a retracted position to an extended position; and decoupling the lancet from the drive member through at least a portion of a path of forward travel of the lancet by impacting the drive member, but not the lancet, against a drive member stop member before the lancet reaches the extended position so that the drive member stops its forward travel and the lancet continues its forward travel under its own momentum towards the extended position, wherein the drive member decouples from the lancet from before the lancet reaches the extended position at least until the lancet is in the extended position so that the mass of the drive member is not bearing on the lancet when the lancet lances the skin.

17. The method of claim 16, further comprising stopping the lancet in the extended position by impacting the lancet against a lancet stop member that is separate from the drive member stop member.

18. The method of claim 16, further comprising providing a lancing device comprising the lancet and the drive member.

* * * * *